(12) United States Patent
Ludwig et al.

(10) Patent No.: US 10,493,290 B2
(45) Date of Patent: Dec. 3, 2019

(54) ENHANCED WEARABLE THERAPY DEVICE PAIRED WITH INSERTABLE CARDIAC MONITOR

(71) Applicant: Cardiac Pacemakers, Inc., St. Paul, MN (US)

(72) Inventors: Jacob M. Ludwig, Isanti, MN (US); Ron A. Balczewski, Bloomington, MN (US); Todd W. Grotbeck, Woodbury, MN (US); Keith R. Maile, New Brighton, MN (US); Moira B. Sweeney, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 15/282,105

(22) Filed: Sep. 30, 2016

(65) Prior Publication Data
US 2017/0095673 A1     Apr. 6, 2017

Related U.S. Application Data

(60) Provisional application No. 62/236,645, filed on Oct. 2, 2015.

(51) Int. Cl.
*A61N 1/39* (2006.01)
*A61B 5/00* (2006.01)
(Continued)

(52) U.S. Cl.
CPC ............ *A61N 1/3987* (2013.01); *A61B 5/002* (2013.01); *A61B 5/0006* (2013.01);
(Continued)

(58) Field of Classification Search
CPC ... A61B 5/0402; A61B 5/4836; A61B 5/0245; A61B 5/0006; A61B 5/0002;
(Continued)

(56) References Cited

U.S. PATENT DOCUMENTS

| 7,974,689 B2 | 7/2011 | Volpe et al. |
| 7,991,467 B2 * | 8/2011 | Markowitz ............ A61N 1/025 607/14 |

(Continued)

FOREIGN PATENT DOCUMENTS

| WO | WO9839061 A2 | 9/1998 |
| WO | 2007076435 A2 | 7/2007 |
| WO | 2008020369 A1 | 2/2008 |

OTHER PUBLICATIONS

International Search Report and Written Opinion issued in PCT/US2016/054830, dated Jan. 16, 2017, 14 pages.

*Primary Examiner* — Deborah L Malamud
(74) *Attorney, Agent, or Firm* — Faegre Baker Daniels, LLP (57) ABSTRACT

A medical system for providing a defibrillation therapy to a patient includes a cardiac monitoring device (CMD) configured to sense and record physiological data indicative of the patient's cardiac function. The CMD includes a communication component. The system also includes an external therapy device configured to deliver defibrillation therapy, and configured to be positioned external to and supported by the patient. The external therapy device includes an external therapy device communication component. The CMD communication component and the external therapy device communication component are configured to operatively couple the CMD and the external therapy device to one another, so as to work as a system to detect and treat fibrillation.

9 Claims, 6 Drawing Sheets

(51) Int. Cl.
*A61B 5/046* (2006.01)
*A61B 5/0464* (2006.01)
*A61B 5/0408* (2006.01)
*A61B 5/042* (2006.01)
*A61B 5/0205* (2006.01)
*A61B 5/08* (2006.01)
*A61B 5/11* (2006.01)
*G16H 50/30* (2018.01)

(52) U.S. Cl.
CPC ............ *A61B 5/0031* (2013.01); *A61B 5/042* (2013.01); *A61B 5/046* (2013.01); *A61B 5/0408* (2013.01); *A61B 5/0464* (2013.01); *A61B 5/6805* (2013.01); *A61B 5/686* (2013.01); *A61B 5/7264* (2013.01); *A61B 5/7275* (2013.01); *A61N 1/3925* (2013.01); *A61B 5/0205* (2013.01); *A61B 5/0816* (2013.01); *A61B 5/1102* (2013.01); *A61B 5/1116* (2013.01); *A61B 5/4836* (2013.01); *A61B 2505/01* (2013.01); *A61B 2560/0443* (2013.01); *A61B 2560/0468* (2013.01); *G16H 50/30* (2018.01)

(58) Field of Classification Search
CPC ... A61B 5/6804; A61B 5/686; A61B 5/02438; A61B 5/04012; A61B 5/6801; A61B 5/6831; A61B 5/6833; A61B 5/0031; A61B 5/00; A61B 5/04; A61B 5/486; A61N 1/046; A61N 1/0484; A61N 1/3625; A61N 1/39; A61N 1/3968; A61N 1/362; A61N 1/37217; A61N 1/3975; A61N 1/0472; A61N 1/00; A61N 1/025; A61N 1/0504; A61N 1/0563; A61N 1/08; A61N 1/36; A61N 1/36014; A61N 1/3702; A61N 1/37235; A61N 1/3904; G06F 19/3418; G06F 19/3406; G06F 1/163; H04L 67/12; A41D 13/1281; A41D 1/002; Y10S 901/46

See application file for complete search history.

(56) References Cited

U.S. PATENT DOCUMENTS

| | | |
|---|---|---|
| 2004/0133242 A1 | 7/2004 | Chapman et al. |
| 2006/0173498 A1 | 8/2006 | Banville et al. |
| 2009/0005827 A1 | 1/2009 | Weintraub et al. |
| 2010/0241181 A1 | 9/2010 | Savage et al. |
| 2011/0288604 A1 | 11/2011 | Kaib et al. |
| 2014/0100622 A1 | 4/2014 | Sullivan et al. |
| 2015/0005588 A1 | 1/2015 | Herken et al. |
| 2015/0217121 A1 | 8/2015 | Subramanian et al. |

\* cited by examiner

ENHANCED WEARABLE THERAPY DEVICE PAIRED WITH INSERTABLE CARDIAC MONITOR

CROSS-REFERENCE TO RELATED APPLICATION

This application claims priority to Provisional Application No. 62/236,645, filed Oct. 2, 2015, which is herein incorporated by reference in its entirety.

TECHNICAL FIELD

Aspects of this disclosure relate to medical devices and methods for treating cardiac fibrillation. More specifically, embodiments relate to medical systems including for paired cardiac monitors and wearable cardiac defibrillators, and methods of using such systems.

BACKGROUND

Arrhythmia detection and classification in existing Wearable Cardiac Defibrillators (WCDs) can be challenging, as therapy decisions must be made based on surface electrocardiograms (ECGs) as opposed to the intra-cardiac signals typical to Implantable Cardioverter Defibrillators (ICDs). As such, conventional WCDs typically include patient-activated "abort" features that allow the wearer to prevent the device from delivering a defibrillation shock in the event the WCD has falsely detected an arrhythmia. Detection specificity requirements for WCDs are also greater than those of Automated External Defibrillators (AEDs) because the WCD is worn continuously, whereas the AED is only applied when a patient demonstrates obvious symptoms of an arrhythmia. Accordingly, there is a continuing need for improved wearable defibrillation systems that have high sensitivity for detecting arrhythmias requiring therapy delivery, and which also reduce the occurrence of inappropriate therapy delivery.

SUMMARY

In an Example 1, a medical system for providing a defibrillation therapy to a patient, the system comprises a cardiac monitoring device (CMD) configured to sense and record physiological data indicative of the patient's cardiac function, the CMD including control circuitry, data storage circuitry, at least one sensing electrode operatively coupled to the control circuitry, a CMD communication component, and a power source coupled to the control circuitry and the CMD communication component; an external therapy device configured to deliver the defibrillation therapy, the external therapy device configured to be positioned external to and supported by the patient and including an external therapy device communication component; wherein the CMD communication component and the external therapy device communication component are configured to operatively couple the CMD and the external therapy device to one another.

In an Example 2, the medical system of Example 1, wherein the control circuitry of the CMD is configured to detect and classify a cardiac arrhythmia based on patient cardiac activity sensed by the at least one sensing electrode of the CMD.

In an Example 3, the medical system of Example 2, wherein the CMD is configured to transmit, via the CMD communication component, a signal to the external therapy device based on the arrhythmia detected and classified by the control circuit of the CMD.

In an Example 4, the medical system of Example 3, wherein the signal includes a command signal directing the external therapy device to deliver the defibrillation therapy to the patient.

In an Example 5, the medical system of any of Examples 1-4, wherein the external therapy device is configured to transmit, via the external therapy device communication component, a query to the CMD in response to the external therapy device detecting and classifying a treatable arrhythmia, and wherein the signal includes an abort command or an arrhythmia confirmation signal.

In an Example 6, the medical system of any of Examples 3-5, wherein the CMD further comprises at least one sensor configured to provide to the control circuitry of the CMD data regarding a patient physiological parameter, and wherein the control circuitry of the CMD is configured to detect and classify the cardiac arrhythmia based at least in part on the data provided by the sensor.

In an Example 7, the medical system of Example 6, wherein the at least one sensor includes at least one of an accelerometer and a posture sensor.

In an Example 8, the medical system of any of Examples 1-7, wherein the CMD is configured to be implanted subcutaneously in the patient.

In an Example 9, the medical system of any of Examples 1-8, wherein the CMD communication component and the external therapy device communication component are configured to operatively couple the CMD and the external therapy device to one another over a wireless communication link.

In an Example 10, the medical system of Example 9, wherein the wireless communication link is a radiofrequency (RF) telemetry link.

In an Example 11, the medical system of any of Examples 1-7, wherein the CMD is configured to be positioned external to the patient, and wherein the at least one sensing electrode of the CMD is configured to be in electrical communication with the patient's skin.

In an Example 12, the medical system of Example 11, wherein the CMD communication component and the external therapy device communication component are configured to operatively couple the CMD and the external therapy device to one another over at least one of a wireless and a wired communication link.

In an Example 13, a method of treating a cardiac arrhythmia in a patient comprises detecting and classifying, by a first medical device coupled to the patient, the cardiac arrhythmia; sending, by the first medical device, a signal to a second medical device coupled to the patient based on the detection of the cardiac arrhythmia, including sending the signal over a communication link operatively coupling the first and second medical devices, wherein the signal includes a therapy delivery command if the first medical device classifies the arrhythmia as a treatable arrhythmia; and selecting, by one of the first and second medical devices, a therapy response to the signal from the first medical device, wherein the response includes aborting delivery of a defibrillation shock to the patient if the signal is an abort command, and delivering the defibrillation shock to the patient if the signal is a confirmation that the first medical device has classified the cardiac arrhythmia as treatable.

In an Example 14, a method of treating a cardiac arrhythmia in a patient comprises detecting, by an external defibrillation device coupled to and supported by the patient, a cardiac arrhythmia; querying a cardiac monitoring device that is separate from and operatively coupled to the external defibrillation device and operatively coupled to and supported by the patient, including requesting a confirmation that the detected arrhythmia is treatable by the external defibrillation device, wherein the query is transmitted over a communication link operatively coupling the cardiac monitoring device to the external defibrillation device; transmitting, by the cardiac monitoring device, a response signal responsive to the query from the external defibrillation device, wherein the response is transmitted over the communication link; delivering, by the external defibrillation device, a therapeutic shock to the patient if the response signal from the cardiac monitoring device includes a confirmation that the detected cardiac arrhythmia is treatable; and selecting a second therapy option if the response signal does not include a confirmation that the detected cardiac arrhythmia is treatable.

In an Example 15, the method of Example 14, wherein the cardiac monitoring device is positioned external to and supported by the patient.

In an Example 16, a medical system for providing a defibrillation therapy to a patient comprises a cardiac monitoring device (CMD) configured to sense and record physiological data indicative of the patient's cardiac function, the CMD including control circuitry, data storage circuitry, a sensing electrode operatively coupled to the control circuitry, a CMD communication component, and a power source coupled to the control circuitry and the CMD communication component; a wearable cardiac defibrillator device (WCD) configured to deliver the defibrillation therapy, the WCD configured to be positioned external to and supported by the patient and including a WCD communication component; wherein the CMD communication component and the WCD communication component are configured to operatively couple the CMD and the WCD to one another.

In an Example 17, the medical system of Example 16, wherein the control circuitry of the CMD is configured to detect and classify a cardiac arrhythmia based on patient cardiac activity sensed by the sensing electrode of the CMD.

In an Example 18, the medical system of Example 17, wherein the CMD is configured to transmit, via the CMD communication component, a signal to the WCD based on the arrhythmia detected and classified by the control circuit of the CMD.

In an Example 19, the medical system of Example 18, wherein the signal includes a command signal directing the WCD to deliver the defibrillation therapy to the patient.

In an Example 20, the medical system of Example 17, wherein the WCD is configured to transmit, via the WCD communication component, a query to the CMD in response to the WCD detecting and classifying a treatable arrhythmia, and wherein the signal includes an abort command or an arrhythmia confirmation signal.

In an Example 21, the medical system of Example 18, wherein the CMD further comprises at least one sensor configured to provide to the control circuitry of the CMD data regarding a patient physiological parameter, and wherein the control circuitry of the CMD is configured to detect and classify the cardiac arrhythmia based at least in part on the data provided by the sensor.

In an Example 22, the medical system of Example 21, wherein the at least one sensor includes at least one of an accelerometer and a posture sensor.

In an Example 23, the medical system of Example 18, wherein the CMD is configured to be implanted subcutaneously in the patient.

In an Example 24, the medical system of Example 23, wherein the CMD communication component and the WCD communication component are configured to operatively couple the CMD and the WCD to one another over a wireless communication link.

In an Example 25, the medical system of Example 24, wherein the wireless communication link is a radiofrequency (RF) telemetry link.

In an Example 26, the medical system of Example 18, wherein the CMD is configured to be positioned external to the patient, and wherein the sensing electrode of the CMD is configured to be in electrical communication with the patient's skin.

In an Example 27, the medical system of Example 26, wherein the CMD communication component and the WCD communication component are configured to operatively couple the CMD and the WCD to one another over at least one of a wireless and a wired communication link.

In an Example 28, a method of treating a cardiac arrhythmia in a patient comprises detecting and classifying, by a first medical device coupled to the patient, the cardiac arrhythmia; sending, by the first medical device, a signal to a second medical device coupled to the patient based on the detection of the cardiac arrhythmia, including sending the signal over a communication link operatively coupling the first and second medical devices, wherein the signal includes a therapy delivery command if the first medical device classifies the arrhythmia as a treatable arrhythmia; and selecting, by one of the first and second medical devices, a therapy response to the signal from the first medical device, wherein the response includes aborting delivery of a defibrillation shock to the patient if the signal is an abort command, and delivering the defibrillation shock to the patient if the signal is a confirmation that the first medical device has classified the cardiac arrhythmia as treatable.

In an Example 29, a method of treating a cardiac arrhythmia in a patient comprises detecting, by an external defibrillation device coupled to and support by the patient, a cardiac arrhythmia; querying a cardiac monitoring device that is separate from and operatively coupled to the external defibrillation device and operatively coupled to and supported by the patient, including requesting a confirmation that the detected arrhythmia is treatable by the external defibrillation device, wherein the query is transmitted over a communication link operatively coupling the cardiac monitoring device to the external defibrillation device; transmitting, by the cardiac monitoring device, a response signal responsive to the query from the external defibrillation device, wherein the response is transmitted over the communication link; delivering, by the external defibrillation device, a therapeutic shock to the patient if the response signal from the cardiac monitoring device includes a confirmation that the detected cardiac arrhythmia is treatable; and selecting a second therapy option if the response signal does not include a confirmation that the detected cardiac arrhythmia is treatable.

In an Example 30, the method of Example 29, wherein the cardiac monitoring device is positioned external to and supported by the patient.

In an Example 31, the method of Example 29, wherein the cardiac monitoring device is implanted subcutaneously in the patient, and wherein the communication link is a wireless communication link.

In an Example 32, the method of Example 29, further comprising, prior to transmitting the response signal, the cardiac monitoring device analyzing patient cardiac activity data obtained from a sensing electrode disposed within the cardiac monitoring device and coupled to the patient to confirm the occurrence of the cardiac arrhythmia.

In an Example 33, the method of Example 32, further comprising, in response to the cardiac monitoring device confirming the occurrence of the cardiac arrhythmia, the cardiac monitoring device classifying the cardiac arrhythmia as either treatable or non-treatable by the external defibrillation device.

In an Example 34, the method of Example 33, wherein the second therapy option includes withholding delivery of the therapeutic shock if the response signal indicates that the cardiac monitoring device has classified the arrhythmia as non-treatable.

In an Example 35, the method of Example 33, wherein the second therapy option includes the cardiac monitoring device or the external defibrillation device performing a therapy decision-making algorithm if the response signal indicates that the cardiac monitoring device has classified the arrhythmia as non-treatable, and either delivering the therapeutic shock or withholding delivery of the therapeutic shock in response to the performance of the therapy decision-making algorithm.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

While the disclosed subject matter is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

DETAILED DESCRIPTION

Figure 1:
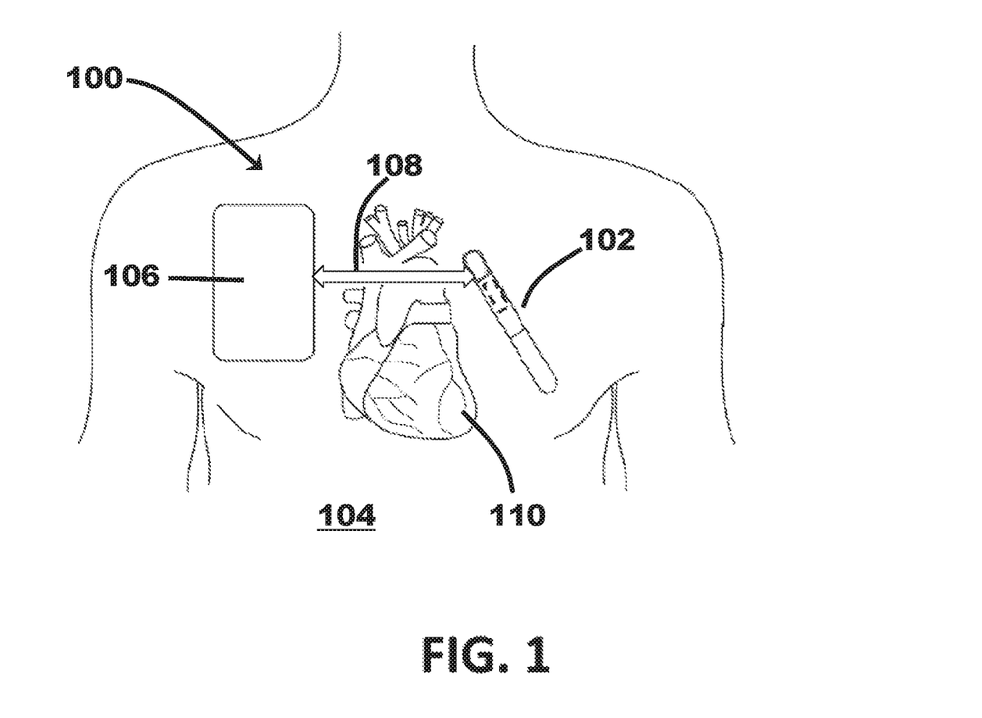
FIG. 1 is a schematic illustration of a medical system including a cardiac monitoring device (CMD) and a wearable cardiac defibrillator (WCD), in accordance with embodiments of the disclosure.

FIG. 1 is a schematic illustration of a medical system 100 including a cardiac monitoring device (CMD) 102 and an external therapy device 106, which is communicatively coupled to the CMD 102 via a communication link 108. In the illustrated embodiments, the medical system 100 is operatively coupled to a patient 104, and the CMD 102 and the therapy device 106 are configured to communicate with one another over the communication link 108. The patient 104 may be a human, a dog, a pig, and/or any other animal having physiological parameters that can be recorded. In various embodiments, as explained in further detail below, the CMD 102 may be implanted subcutaneously within an implantation location or pocket in the patient's chest or abdomen, while in other embodiments, the CMD 102 may be a wearable device that is configured to be worn by the patient 104, e.g., by being integrated into a vest, belt, harness, sticker, and/or the like, and may be configured to monitor (e.g., sense and/or record) physiological parameters associated with the patient's heart 110. In embodiments, the CMD 102 may be an implantable cardiac monitor (ICM) (e.g., an implantable diagnostic monitor (IDM), an implantable loop recorder (ILR), etc.). In any of the foregoing embodiments, the CMD 102 may be configured to record physiological parameters such as, for example, one or more cardiac activation signals, heart rate, heart rhythms, heart sounds, blood pressure measurements, oxygen saturations, and/or the like.

In embodiments, the CMD 102 may be configured to monitor physiological parameters that may include one or more signals indicative of a patient's physical activity level and/or metabolic level, such as an acceleration signal. In embodiments, the CMD 102 may be configured to monitor physiological parameters associated with one or more other organs, systems, and/or the like. The CMD 102 may be configured to sense and/or record at regular intervals, continuously, and/or in response to a detected event. In embodiments, such a detected event may be detected by one or more sensors of the CMD 102 and/or the wearable therapy device 106. In addition, the CMD 102 may be configured to detect a variety of physiological signals that may be used in connection with various diagnostic, therapeutic and/or monitoring implementations. For example, the CMD 102 may include sensors and/or circuitry for detecting respiratory system signals, cardiac system signals, heart sounds, and/or signals related to patient activity. In embodiments, the CMD 102 may be configured to sense intrathoracic impedance, from which various respiratory parameters may be derived, including, for example, respiratory tidal volume and minute ventilation. Sensors and associated circuitry may be incorporated in connection with the CMD 102 for detecting one or more body movement or body posture and/or position related signals. For example, accelerometers and/or GPS devices may be employed to detect patient activity, patient location, body orientation, and/or torso position.

In various embodiments, the external therapy device 106 may include any type of therapy device (e.g., a defibrillation device) capable of being worn by, or otherwise operatively coupled to, the patient and to deliver one or more defibrillation shocks upon the detection of a potentially life-threatening cardiac arrhythmia. For example, the external therapy device 106 may be a wearable cardiac defibrillator (WCD) such as a vest that includes one or more defibrillation electrodes. In embodiments, the external therapy device 106 may include sensing components such as, for example, one or more surface electrodes configured to obtain an electrocardiogram (ECG), one or more accelerometers configured to detect motion associated with the patient 104, one or more respiratory sensors configured to obtain respiration information, one or more environmental sensors configured to obtain information about the external environment (e.g., barometric pressure, temperature, relative humidity, and/or the like) surrounding the patient 104, and/or the like. According to embodiments, the external therapy device 106 may be a conventional WCD such as are currently known, modified in accordance with embodiments of the present disclosure. Examples of such conventional WCDs include the systems described in U.S. Pat. No. 7,974,689 and U.S.

Patent Publication No. 2015/0005588, the disclosure of each of which is incorporated herein. It is emphasized, however, that the foregoing WCD systems are merely exemplary only, and the present disclosure is in no way limited to incorporation of those systems.

In various embodiments, the external therapy device 106 may be operatively coupled to the patient 104, and/or may be, may include, or may be included in a vest, a belt, a strap, a harness, a sticker, and/or the like. In embodiments, the external therapy device 106 may include any number of different therapy components in addition to a defibrillation therapy component such as, for example, a drug delivery component, a neurostimulation component, a neuromodulation component, a temperature regulation component, and/or the like. In embodiments, the external therapy device 106 may include limited functionality, e.g., defibrillation shock delivery and communication capabilities, with arrhythmia detection, classification and/or therapy command/control being performed by a separate device such as, for example, the CMD 102.

In various embodiments, the CMD 102 and the external therapy device 106 are operatively paired via the communication link 108, such that the CMD 102's physiologic parameter sensing, arrhythmia detection and/or classification capabilities can be used to control and/or support the delivery of defibrillation shocks by the external therapy device 106. In various embodiments, the defibrillation therapy command/control may be performed entirely in the CMD 102, with the external therapy device 106 operating primarily as a therapy delivery device. In other embodiments, therapy control is performed by the external therapy device 106, and the CMD 102 operates to provide enhanced sensing and/or arrhythmia detection capabilities to the medical system 100, such that the confidence that a potentially life-threatening arrhythmia is present can be enhanced prior to delivery of a defibrillation shock, or alternatively, to override the arrhythmia determinations made by the external therapy device 106 and abort the therapy delivery. According to embodiments, any number of schemes for distributing functionality between the CMD 102 and the external therapy device 106 may be implemented. In embodiments, one or more operations may be performed by an additional device and/or system not illustrated. For example, in embodiments, the CMD 102 and/or the external therapy device 106 may provide physiologic information, via a communication link, to an implanted device, external device, backend computing system, patient monitoring system, network, and/or the like, for processing, presentation to a clinician and/or other user, event classification, and/or the like.

Figure 2A:
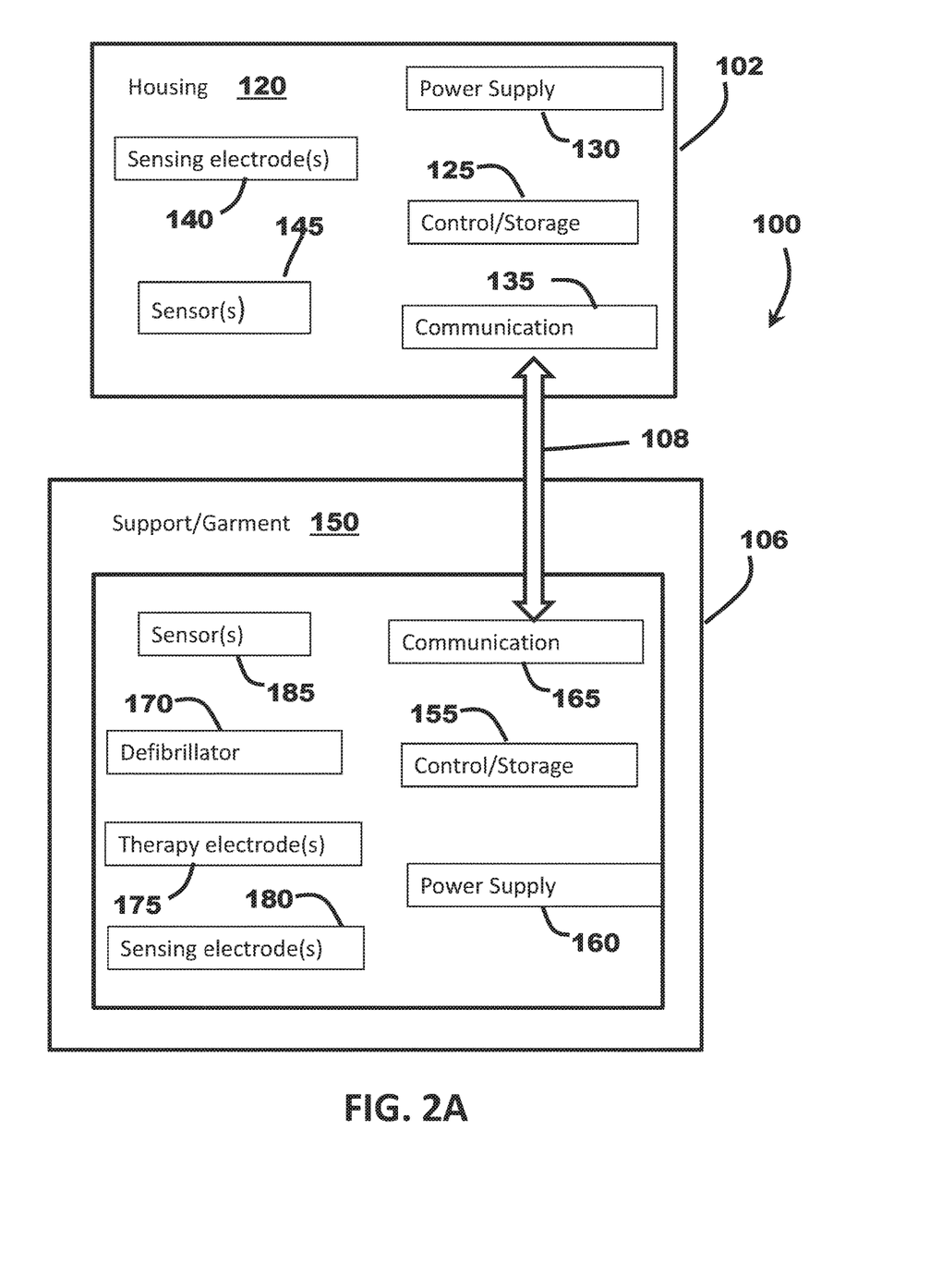
FIG. 2A is a block diagram of aspects of the medical system of FIG. 1, in accordance with embodiments of the disclosure.

FIG. 2A is a schematic block diagram of embodiments of the medical system 100 in which the CMD 102 is an implantable cardiac monitor (ICM) as described above, and the communication link 108 is a wireless communication link.

In the illustrated embodiments, the implantable CMD 102 may be implanted subcutaneously within an implantation location or pocket in the patient's chest or abdomen and may be configured to monitor (e.g., sense and/or record) physiological parameters associated with the patient's heart. In embodiments, the implantable CMD 102 may be positioned in a subcutaneous pocket formed in or near the patient's chest or abdomen. In embodiments, the implantable CMD 102 may be deployable to a subcutaneous location via a syringe or similar instrumentation, i.e., not requiring an implantation pocket be separately formed. Any subcutaneously implanted CMD 102, whether now known or later developed, may be utilized within the scope of the present disclosure.

In embodiments, the external therapy device 106 may include a support/garment 150 that supports the external therapy device 106's other functional components, as will be discussed in greater detail elsewhere herein. In various embodiments, the support/garment 150 may be in the shape of a vest or shirt, and may also include at least one belt that may be worn about a subject's waist, at a higher location about the subject's chest, or at other locations between the subject's waist and shoulders. Components of the external therapy device 106, including the support/garment 150, may be worn under, over, or partially under and partially over a subject's clothes.

In the illustrated embodiments, the CMD 102 may include a housing 120 enclosing control/storage circuitry 125, a power supply 130, a communication component 135, a sensing electrode 140, and optionally additional sensors 145, any combination of which may be operatively interconnected to one another within the housing 120. While, for simplicity, the block diagram of FIG. 2A shows single blocks designating the sensing electrode 140 and the sensors 145, in various embodiments, the CMD 102 may include any number of electrodes 140 as well as any number of sensors 145.

The control/storage circuitry 125 may be any arrangement of electronic circuits and components configured to store and/or execute programming instructions, to direct the operation of the other functional components of the CMD 102, to perform arrhythmia detection and/or classification algorithms, to store physiologic data received by the sensing electrode(s) 140 and/or the additional sensor(s) 145, and/or the like, and may be implemented, for example, in the form of any combination of hardware, software, and/or firmware. The skilled artisan would readily appreciate the types of control and storage circuitry that may be employed in the control/storage circuitry 125 based on the present disclosure (e.g., processors, memory devices, circuits, and/or the like), and therefore the control/storage circuitry need not be discussed in greater detail herein.

The power supply 130 provides electrical power to the other operative components (e.g., the control/storage circuitry 125, the communication component 135 and/or the sensors 145), and can be any type of power supply suitable for providing the desired performance and/or longevity requirements of the system 100. In various embodiments, the power supply 130 may be a battery, which may be rechargeable using an external energy source. Power supplies for medical devices such as the CMD 102 are well known, and are therefore not discussed in greater detail herein.

In embodiments, the sensing electrode(s) 140 may be configured to sense intrinsic cardiac electrical signals in a manner similar to known electrocardiogram (ECG) electrodes, which signals are transmitted via conventional techniques to the control/storage circuitry 125. In embodiments, the specific construction of the sensing electrode(s) 125 is not critical to the various embodiments so long as the electrode(s) 125 can perform the aforementioned sensing function.

In various embodiments, the additional sensor(s) 145 may be provided to sense other patient physiologic or environmental parameters in addition to the cardiac signals sensed by the sensing electrode(s) 140. In embodiments, the additional sensor(s) 145 may include temperature sensors (e.g., thermocouples or thermistors), barometers, acoustic sensors, pressure sensors, optical sensors, motion or impact sensors (e.g., accelerometers), and/or the like) in any number of various types of configurations. The foregoing sensors allow the CMD 102 to be capable of sensing and recording physiologic parameters such as, for example, patient movement, posture, respiratory cycles, heart sounds, and/or the like. The output from each such sensor 145 can be transmitted to the control/storage circuitry 125 for use in arrhythmia detection and classification and/or therapy selection.

In various embodiments, the CMD 102 may be configured to perform arrhythmia detection and/or classification algorithms based on the sensed and recorded cardiac signals and, where provided, the additional physiologic data described previously. In such embodiments, the CMD 102 may be configured to determine if the patient is (or is not) experiencing a potentially life-threatening arrhythmia such as ventricular fibrillation, and may provide an output to the external therapy device 106 in response to such a determination. In various embodiments, this output from the CMD 102 may include a command for the external therapy device 106 to deliver a defibrillation shock to the patient to terminate the arrhythmia. In embodiments, this output from the CMD 102 may include a confirmation that an arrhythmia detected by the external therapy device 106 is, or is not, a potentially life-threatening arrhythmia warranting intervention by the external therapy device 106. The particular arrhythmia detection algorithm(s) employed by the CMD 102 are not critical to any particular embodiments. Rather, numerous such algorithms are well known in the art, and thus need not be discussed in greater detail herein.

In embodiments, the CMD 102 may be configured to assess the operation of the external therapy device 106 and provide corresponding information to a clinician and/or use this information in the CMD 102's arrhythmia detection and/or therapy decision operations. For example, in embodiments, the control/storage circuitry 125 may be configured to determine skin impedance between the sensing electrodes 140 and the patient's skin, and compare this measured impedance with that of the external therapy device 106's electrodes (discussed below) to diagnose poor contact between the external therapy device 106's sensing electrode(s) and the skin. Also, in some embodiments, the control/storage circuitry 125 may be configured to determine the impedance between the sensing electrodes 140 and the patient's skin, to diagnose poor contact between the sensing electrodes 140 and the patient's skin and to validate or invalidate the CMD's 102 rhythm classification based on this information. Also, in some embodiments, the external therapy device 106 may be configured to determine the impedance between the external therapy device 106's electrodes and the patient's skin, to diagnose poor contact between the external therapy device 106's electrodes and the patient's skin.

In the illustrated embodiments, the external therapy device 106 includes control/storage circuitry 155, a power supply 160, a communication component 165, a defibrillator 170, therapy electrode(s) 175, sensing electrode(s) 180 and optionally additional sensors 185, which are mounted to the support/garment 150.

Similar to the CMD 102, the control/storage circuitry 155 may be any arrangement of electronic circuits and components configured to store and execute programming instructions, to direct the operation of the other functional components of the external therapy device 106, to perform arrhythmia detection and/or classification algorithms, to store physiologic data received by the sensing electrode(s) 180 and the additional sensor(s) 185, and/or the like, and may be implemented using any combination of hardware, software, and/or firmware. The skilled artisan would readily appreciate the types of control and storage circuitry that may be employed in the control/storage circuitry 155 based on the present disclosure, and therefore the control/storage circuitry need not be discussed in greater detail herein.

The power supply 160 provides electrical power to the other operative components (e.g., the control/storage circuitry 155, the communication component 165, the defibrillator 170 and therapy electrode(s) 175, and/or the additional sensors 185), and can be any type of power supply suitable for providing the desired performance and/or longevity requirements of the system 100. In various embodiments, the power supply 160 may be a battery, which may be rechargeable using an external energy source. Power supplies for medical devices such as the external therapy device 102 are well known, and are therefore not discussed in greater detail herein.

The defibrillator 170 is electrically coupled to the therapy electrode(s) 175 so as to be configured to deliver a therapeutic electrical shock to the patient to terminate a detected ventricular fibrillation condition. When such a shock is applied, the therapy electrodes 175, the patient's body, and the defibrillator 170 form at least part of a current path. For example, one embodiment includes at least one sensing electrode 180, one therapy electrode 175 disposed in front of the subject, e.g., proximate to the patient's chest, and two therapy electrodes 175 disposed in back of the patient, e.g. proximate to the patient's back.

The support/garment 150 is configured to hold the electrodes 175, 180 in position, for example against the patient's skin around the patient's torso. When positioned against the patient, the sensing electrode(s) 180 can sense electrocardiogram signals used by the control/storage circuitry 155 to monitor the patient's cardiac activity. When the control/storage circuitry 155 identifies an arrhythmia or other cardiac event, the therapy electrodes 175, when positioned against the patient can deliver defibrillating energy to the patient to convert the arrhythmia to a normal sinus rhythm.

In embodiments, the sensing electrodes 180 and the therapy electrodes 175 are securely positioned against the patient's body in order for the sensing electrodes 180 to sense cardiac, respiratory, or other information about the patient; and for the therapy electrodes 175 to apply treatment to the patient. For example, the sensing electrode 180 may include electrocardiogram electrodes that directly or indirectly (e.g., via clothes, a conductive protective barrier, or a conductive fluid) contact the patient's skin to sense an electrocardiogram signal with minimal artifacts. Further, the therapy electrode 175 may directly or indirectly contact the patient's skin to reduce impedance between the therapy electrode 175 and the patient's skin and to efficiently deliver defibrillating energy to the patient, without causing burns, blisters, inflammation, or other damage to the patient's skin.

In embodiments, the functionality of the defibrillator 170 may be performed at least partially in software executed by at least one processor of the control/storage circuitry 155. In other embodiments, the functionality of the defibrillator 170 may be implemented in a Field Programmable Gate Array (FPGA), one or more Programmable Logic Devices (PLDs), a Complex PLD (CPLD), a custom Application Specific Integrated Circuit (ASIC), and/or a dedicated processor operating under the control of the at least one processor of the control/storage circuitry 155. It should be appreciated that other implementations may be used, as the present disclosure is not limited to any particular implementation.

In embodiments, the external therapy device 106 may include the ability to warn the patient, e.g., by providing an alarm or warning, which may be audio, visual, haptic (e.g., vibrations) or combinations thereof, to alert the patient prior to the defibrillator 170 delivering a shock through the therapy electrode(s) 175. Such an alarm capability gives the patient an opportunity to take some action to prevent the defibrillator 170 from applying the shock. For example, the external therapy device 106 may include an interface having at least one button or touch screen. In this example, the patient can depress a button, indicating that he/she is conscious. In this example, the shock will not be applied while the subject depresses the button for a sufficient amount of time, or until the control/storage circuitry 155 determines that the electrical heart activity of the subject, detected for example by sensing electrode 180, has returned to normal. Continuing with this example, if the subject loses consciousness, the subject will release the button and the defibrillator 170 can apply a shock via the therapy electrodes 175. In other embodiments, the external therapy device 106 may include capability for allowing the patient to abort therapy delivery altogether.

In embodiments, the therapy electrode(s) 175 and/or the sensing electrode(s) 180 are integral, permanent components of support/garment 150. In embodiments, the sensing electrode(s) 180 and the therapy electrode(s) 175 may include conductive surfaces such as a metal plate or foil in a generally circular, ovoid, or quadrilateral shape. In other embodiments, the sensing electrode(s) 180 and/or the therapy electrode(s) 175 include conductive thread woven, sewn, or embroidered into the support/garment 150. The conductive thread may provide connections between any of the sensing electrodes 180 and the control/storage circuitry 155, and/or also between the therapy electrodes 175 and the defibrillator 170.

Similar to the CMD 102, the additional sensor(s) 185 may be provided to sense other patient physiologic or environmental parameters in addition to the cardiac signals sensed by the sensing electrode(s) 180. In embodiments, the additional sensor(s) 185 may include temperature sensors (e.g., thermocouples or thermistors), barometers, pressure sensors, optical sensors, motion sensors (e.g., accelerometers), and/or the like) in any number of various types of configurations. The foregoing sensors allow the external therapy device 106 to be capable of sensing and recording physiologic parameters such as, for example, patient movement, posture, respiratory cycles, perspiration and/or the like. The output from each such sensor 185 can be transmitted to the control/storage circuitry 155 for use in arrhythmia detection and/or classification and/or therapy selection.

In the illustrated embodiments, the communication components 135, 165 operate to facilitate communication between the CMD 102 and the external therapy device 106 through the wireless communication link 108.

In embodiments, the communication link 108 may be a short-range radio link, such as Bluetooth, IEEE 802.11, a proprietary wireless protocol, and/or the like. In embodiments, for example, the communication link 108 utilizes Bluetooth Low Energy radio (Bluetooth 4.1), or a similar protocol, and may utilize an operating frequency in the range of 2.40 to 2.48 GHz. The communication link 108 may facilitate uni-directional and/or bi-directional communication between the CMD 102 and the external therapy device 106. Data and/or control signals may be transmitted between the CMD 102 and the external therapy device 106 to coordinate the functions of the CMD 102 and/or the external therapy device 106.

The communication link 108 may be facilitated, for example, by one or more antennas (not shown) disposed within, integrated with, and/or coupled to the CMD 102. According to embodiments, the antenna(s) may be disposed, at least in part, within the CMD 102, integrated with a portion of the housing 120 of the CMD 102, be, or include, at least a portion of the housing 120 of the CMD 102, and/or the like. In this manner, the communication components 135, 165 may include any combination of hardware, software, and/or firmware configured to facilitate establishing, maintaining, and using the communication link 108. For example, in embodiments, the communication components 135, 165 may include antennas, processors, programming instructions, circuits, and/or the like.

In other embodiments, other forms of wireless telemetry may be utilized for the communication link 108. For example, in embodiments, other RF telemetry technologies may be employed. Alternatively, and/or additionally, inductive telemetry, acoustic telemetry and/or the like may be employed for the communication link 108. In embodiments, conductive telemetry may be employed for the communication link 108, in which case, for example, the communication component 135 may interact with the sensing electrode(s) 140 to transmit and/or receive communications encoded in electrical pulses and the communication component 165 may similarly interact with the therapy electrode(s) 175 and/or the sensing electrode(s) 180 to transmit and/or receive communications.

In embodiments, patient data may be downloaded from one or more of the CMD 102 and the external therapy device 106 periodically and/or on command from a physician using, for example, an external device (not shown) such as a programmer or external receiving device over an additional communication link or links (not shown). The physician and/or the patient may communicate with the CMD 102 and/or the external therapy device 106, for example, to program the devices, to acquire patient data or to initiate, terminate or modify recording and/or therapy.

The illustrative system 100 shown in FIG. 1 is not intended to suggest any limitation as to the scope of use or functionality of embodiments of the subject matter disclosed throughout this document. Neither should the illustrative system 100 be interpreted as having any dependency or requirement related to any single component or combination of components illustrated therein. For example, in embodiments, the illustrative system 100 may include additional components. Additionally, any one or more of the components depicted in FIG. 1 can be, in embodiments, integrated with various ones of the other components depicted therein (and/or components not illustrated). Any number of other components or combinations of components can be integrated with the illustrative system 100 depicted in FIG. 1, all of which are considered to be within the ambit of the disclosure.

Figure 2B:
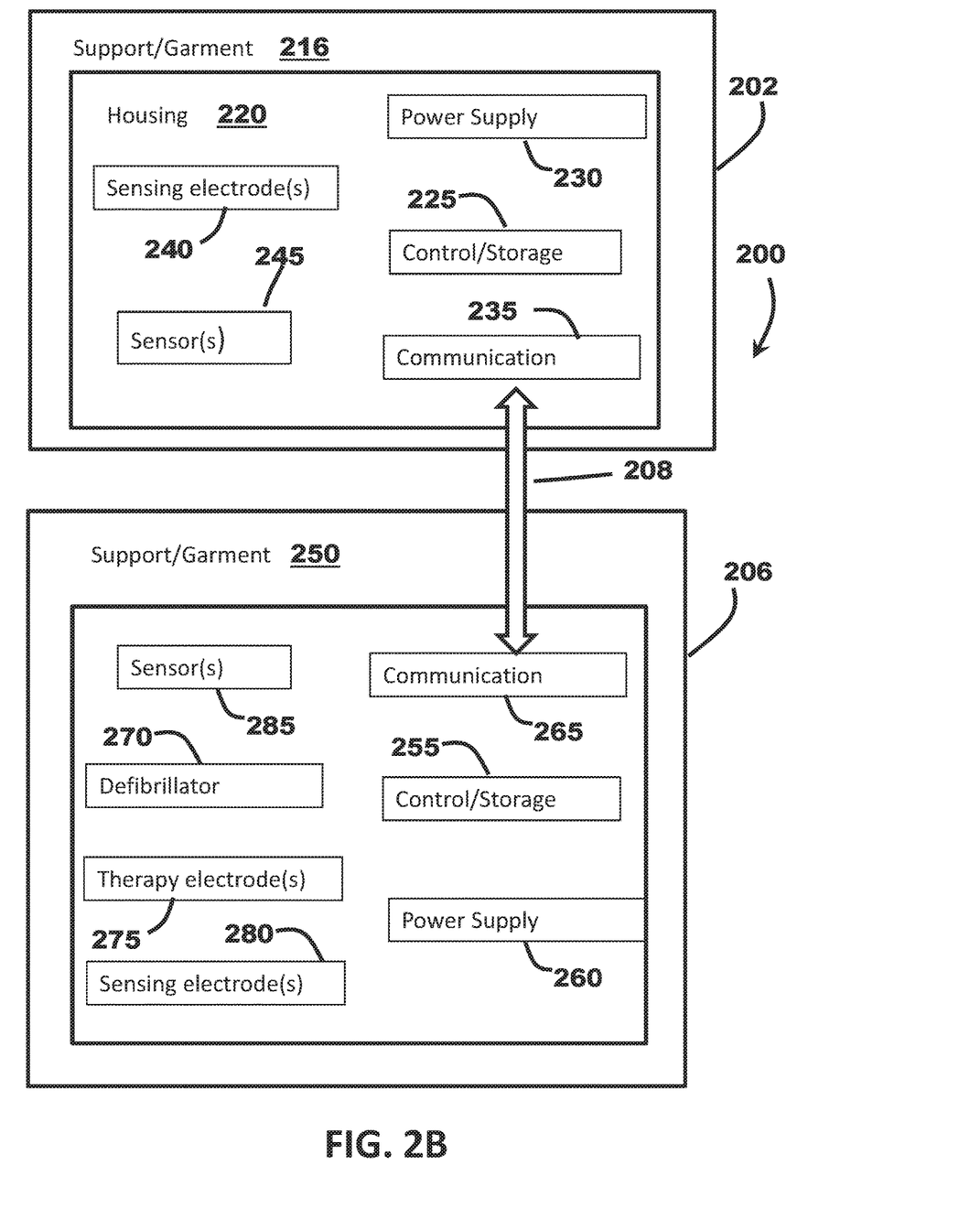
FIG. 2B is a block diagram of a medical system having a wearable cardiac monitoring device and a WCD, in accordance with embodiments of the disclosure.

FIG. 2B is a schematic block diagram of a medical system 200, in accordance with embodiments of the disclosure. In embodiment, the medical system 200 may be substantially similar to embodiments of the medical system 100, and includes a CMD 202 and an external therapy device 206 operatively coupled together via a communication link 208. According to embodiments, the medical system 200 differs from the medical system 100 primarily in that the CMD 202 is a wearable cardiac monitoring device that is not implanted or positioned subcutaneously, but rather is positioned on or adjacent to the patient's skin.

Thus, in the illustrated embodiments, the wearable CMD 202 may include a support/garment 216, a housing 220 enclosing control/storage circuitry 225, a power supply 230, a communication component 235, a sensing electrode 240, and optionally additional sensors 245, any one or more of which may be operatively interconnected to one another within the housing 220. While, for simplicity, the block diagram of FIG. 2B shows single blocks designating the sensing electrode 240 and the sensors 245, in various embodiments, the CMD 202 may include any number of electrodes 240 as well as any number of sensors 245.

In the illustrated embodiments, at least the housing 220, the control/storage circuitry 225, the power supply 230, the communication component 235, the sensing electrode(s) 240, and/or the additional sensor(s) 245 may be substantially the same in design and/or functionality as the corresponding components of the CMD 102. The support/garment 216 operates to support the CMD 202 and allow it to be worn by the patient. In embodiments, the support/garment 216 may be similar in form/function to the support/garment 150 of the external therapy device 106, discussed above. In embodiments, the support/garment 216 is configured to be attachable to, or supported by, the patient's clothing. The specific design of the support/garment 216 is not critical to any particular embodiment of the CMD 202, and thus any number of configurations may be employed within the scope of various embodiments.

The external therapy device 206 may be substantially similar to the external therapy device 106 described previously, and may include control/storage circuitry 255, a power supply 260, a communication component 265, a defibrillator 270, therapy electrode(s) 275, sensing electrode(s) 280 and optionally additional sensors 285, which are mounted to the support/garment 250. In embodiments, at least the garment/support 250, the control/storage circuitry 255, the power supply 260, the communication component 265, the defibrillator 270, the therapy electrode(s) 275, the sensing electrode(s) 280 and/or the additional sensors 285 may be substantially the same as or identical to the corresponding components of the external therapy device 106.

In embodiments, because the CMD 202 is a wearable device, the communication link 208 may be a wired communication link. In such embodiments, a cable may be used to operatively couple the CMD 202 and the external therapy device 206, which are configured to provide ports for connecting the devices via the cable. In such embodiments, the communication components 235, 265 are configured to accommodate direct, wired communication.

In other embodiments, the communication link 208 is a wireless communication link similar to or identical to the wireless communication link 108 described previously in with respect to the medical system 100. In embodiments, the communication link 208 may include a combination of wired and wireless communication links.

Figure 3:
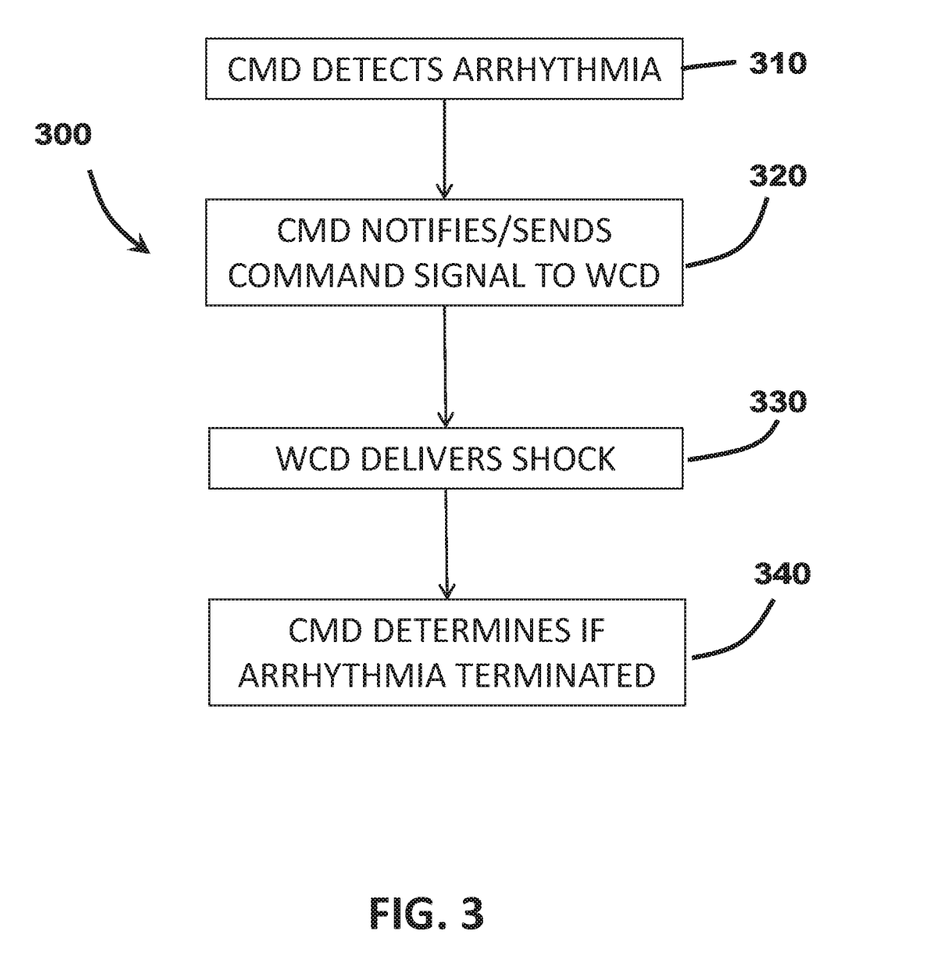
FIGS. 3-5 are flow diagrams illustrating alternative methods of operation of a medical system, in accordance with embodiments of the disclosure.

FIG. 3 is a simplified flow chart schematically illustrating a method 300 of operation for a medical system (e.g., the medical system 100 depicted in FIG. 1 and/or the medical system 200 depicted in FIG. 2), in accordance with embodiments of the disclosure. As shown in FIG. 3, in the illustrated embodiments, the CMD 102 operates as the arrhythmia detection/classification and therapy control device, and directs the operation of the external therapy device 106 (which is implemented, for example in the context of FIG. 3 as a WCD) at least with respect to delivery of therapy to the patient. As such, at Block 310, the CMD 102 detects an arrhythmia requiring treatment, and at Block 320 it notifies the WCD 106 of such and sends the WCD 106 a command signal directing the WCD 106 to deliver a defibrillation shock at Block 330. In embodiments, as further shown, the CMD 102 then determines if the arrhythmia has been terminated (at Block 340).

Figure 4:
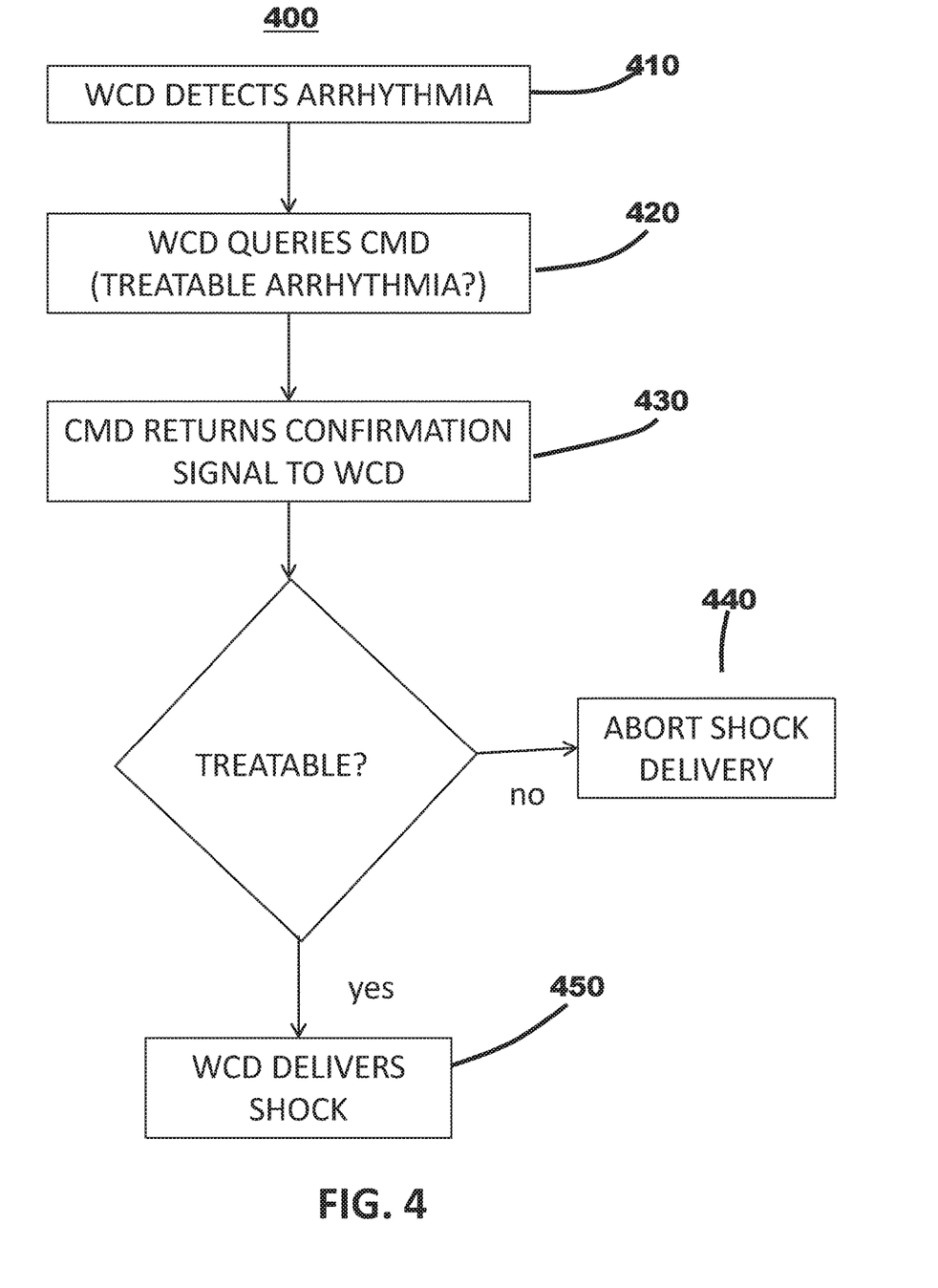

FIG. 4 is a simplified flow chart schematically illustrating a method 400 of operation for a medical system (e.g., the medical system 100 depicted in FIG. 1 and/or the medical system 200 depicted in FIG. 2), in accordance with embodiments of the disclosure. In the method 400, the CMD 102 is again the primary control device with respect to therapy delivery, but both the CMD 102 and the WCD 106 perform arrhythmia detection functions.

As shown in FIG. 4 at Block 410, upon detection of an arrhythmia by the WCD 106, the WCD 106 sends a signal to the CMD 102 querying whether the arrhythmia is treatable (Block 410). The query sent by the WCD 106 may, in various embodiments, include patient data obtained from the sensing electrodes 180 of the WCD 106, as well as other data provided by the additional sensor 185, which may include, for example, posture data, respiratory rates, activity data, and the like. The control/storage circuitry 125 of the CMD 102 may use this data, as well as patient information obtained from the CMD 102's own sensing electrodes and sensors, to determine whether the detected arrhythmia is treatable, and at Block 430 returns a confirmation or abort signal back to the WCD 106 based on this determination.

Thus, as shown at Block 440, if the CMD 102 determines that the detected arrhythmia is not treatable by the WCD 106, it commands the WCD 106 to abort therapy delivery. If, however, the CMD 102 determines that the arrhythmia is treatable by the WCD 106, the CMD 102 sends a confirmation signal that permits the WCD 106 to deliver the therapeutic shock. According to embodiments, upon any of the devices described herein determining and/or confirming that a detected arrhythmia is not treatable, a device may select and/or provide (or send a signal to cause another device to select and/or provide) a second therapy option. A second therapy option may include withholding delivery of the therapeutic shock, providing a different type of therapy such as, for example, a drug therapy, a neurostimulation therapy, and/or the like. In embodiments, the second therapy option may include the cardiac monitoring device and/or the external defibrillation device performing a therapy decision-making algorithm if the response signal indicates that the cardiac monitoring device has classified the arrhythmia as non-treatable, and either delivering the therapeutic shock or withholding delivery of the therapeutic shock in response to the performance of the therapy decision-making algorithm.

In embodiments, to reduce communication timing latencies that may impact the sensitivity of the arrhythmia detection and the confirmation or abort signals, the query by the WCD 106 depicted in Block 410 may be initiated by the WCD 106 starting a communication session via advertising, and then holding the communication link 108 open for a predetermined time period selected to ensure that the CMD 102 can acquire the requisite data, make the arrhythmia determination, and return the confirmation or abort signal to the WCD 106.

Figure 5:
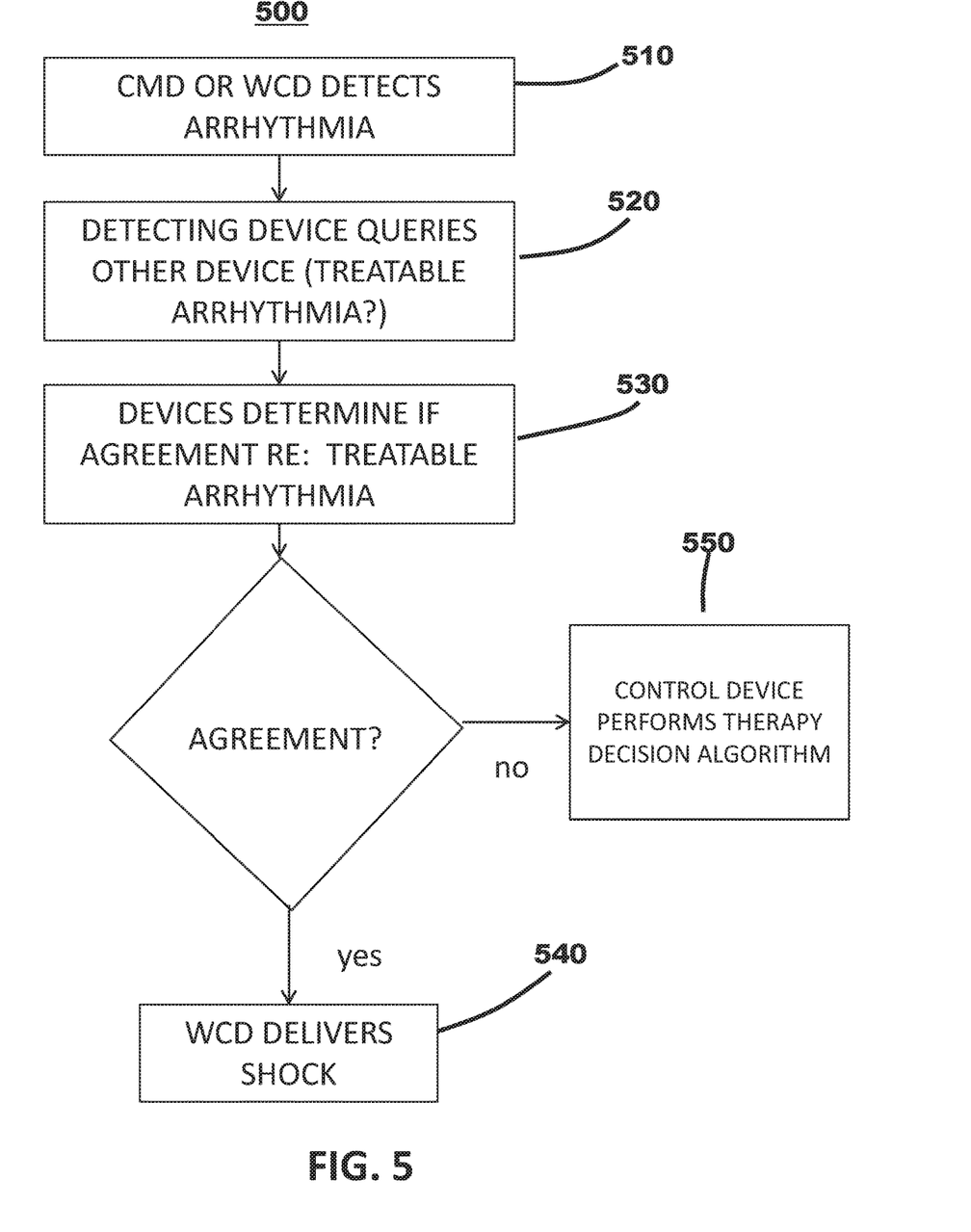

FIG. 5 is a simplified flow chart schematically illustrating another method 500 of operation for a medical system (e.g., the medical system 100 depicted in FIG. 1 and/or the medical system 200 depicted in FIG. 2), in accordance with embodiments of the disclosure. In embodiments, the method 500 is a variation of the method 400 in which both the CMD 102 and the WCD 106 both perform arrhythmia detection and therapy selection functions. In the method 500, as shown, one or both of the CMD 102 and the WCD 106 may detect an arrhythmia (Block 510) and then query the other device to determine whether the arrhythmia is treatable by the WCD 106 (Block 520). Similar to the method 400, the query signal sent by the device that detects the arrhythmia may, in various embodiments, include patient data obtained from the sensing electrodes as well as other data provided by the additional sensors, which may include, for example, posture data, respiratory rates, activity data, and the like. If the devices are in agreement, then the CMD 102 sends a confirmation signal to the WCD 106 over the communication link 108, and the WCD 106 proceeds to deliver the therapy shock (Block 540). If the devices are not in agreement that the detected arrhythmia is treatable, one of the CMD 102 or the WCD 106 is designated as a control device that performs one or more decision-making algorithms to make a final determination as to whether a defibrillation shock should be delivered (Block 550).

According to embodiments, for example, decision-making algorithms may include determining a scoring or confidence metric that may include a characterization confidence associated with the detection from each device. Such metrics may include, for example, signal-to-noise ratios, signal amplitude, and/or the like. Decision-making algorithms may include consideration of additional biological measurements, as well, such as, for example, body position, respiration, heart sounds, and/or the like. For example, one device might detect fibrillation, but may also note very small signal amplitudes. In this case, the device may identify this as a life threatening arrhythmia, but place a "low confidence" tag on the detection. The other device may be detecting large signals, and identify normal rhythm. In this case one device may be suggesting therapy with low confidence, and one device suggesting withholding therapy with high confidence, in which case therapy could be withheld. In another example, one device may detect an arrhythmia and note that respiration has ceased. Therapy might, as a result, be requested with "high confidence." The other device may disagree, but the high confidence therapy request could be considered to overrule the lower confidence request. In embodiments, decision-making algorithms may be, include, or be included in, any number of different types of machine-learning processes such as, for example, supervised and/or unsupervised classifiers, artificial neural networks, and/or the like.

In one embodiment, as with the method 400, to minimize communication timing latencies that may impact the sensitivity of the arrhythmia detection and the confirmation or abort signals, the query by the WCD 106 depicted in Block 510 may be initiated by the WCD 106 starting a communication session via advertising, and then holding the communication link 108 open for a predetermined time period selected to ensure that the CMD 102 can acquire the requisite data, make the arrhythmia determination, perform the therapy decision-making algorithm (if necessary) and return the confirmation or abort signal to the WCD 106.

Although in the foregoing discussion refers to the medical system 100 utilizing an implantable CMD 102, the foregoing methods can be readily utilized by the medical system 202 utilizing a wearable CMD 202.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. A medical system for providing a defibrillation therapy to a patient, the system comprising:
    a cardiac monitoring device (CMD) that is configured to be implanted subcutaneously in the patient and configured to sense and record physiological data indicative of the patient's cardiac function, the CMD including first control circuitry, first data storage circuitry, a CMD sensing electrode operatively coupled to the first control circuitry, a CMD communication component, and a CMD power source coupled to the first control circuitry and the CMD communication component; and
    a wearable cardiac defibrillator device (WCD) configured to deliver the defibrillation therapy, the WCD configured to be positioned external to and supported by the patient and including second control circuitry, second data storage circuitry, a WCD sensing electrode operatively coupled to the second control circuitry, and a WCD communication component;
    the CMD communication component and the WCD communication component are configured to operatively couple the CMD and the WCD to one another, the WCD is configured to: detect an arrhythmia independently of the CMD and, in response to detecting the arrhythmia, transmit a query including patient data obtained by the WCD to the CMD about whether the arrhythmia detected by the WCD is treatable by the WCD; and
    the CMD is configured to: (1) determine, using the patient data transmitted by the WCD, whether the arrhythmia detected by the WCD is treatable by the WCD and, (2) in response to determining that the arrhythmia detected by the WCD is treatable by the WCD, transmit a signal to the WCD that includes a deliver defibrillation therapy command, and (3) in response to determining that the arrhythmia detected by the WCD is not treatable by the WCD, transmit a signal to the WCD that includes an abort command.

2. The medical system of claim 1, wherein the first control circuitry of the CMD is configured to detect and classify a cardiac arrhythmia based on patient cardiac activity sensed by the CMD sensing electrode of the CMD.

3. The medical system of claim 2, wherein the CMD is configured to transmit, via the CMD communication component, the signal to the WCD based on the arrhythmia detected and classified by the first control circuitry of the CMD.

4. The medical system of claim 3, wherein the CMD further comprises at least one sensor configured to provide to the first control circuitry of the CMD data regarding a patient physiological parameter, and wherein the first control circuitry of the CMD is configured to detect and classify the cardiac arrhythmia based at least in part on the data provided by the at least one sensor.

5. The medical system of claim 4, wherein the at least one sensor includes at least one of an accelerometer and a posture sensor.

6. The medical system of claim 1, wherein the CMD communication component and the WCD communication component are configured to operatively couple the CMD and the WCD to one another over a wireless communication link.

7. The medical system of claim 6, wherein the wireless communication link is a radiofrequency (RF) telemetry link.

8. The medical system of claim 3, wherein the CMD is configured to be positioned external to the patient, and wherein the sensing electrode of the CMD is configured to be in electrical communication with the patient's skin.

9. The medical system of claim 8, wherein the CMD communication component and the WCD communication component are configured to operatively couple the CMD and the WCD to one another over at least one of a wireless and a wired communication link.

* * * * *